United States Patent [19]

Damani

[11] 3,971,377

[45] *July 27, 1976

[54] MEDICAMENT DISPENSING PROCESS FOR INHALATION THERAPY

[75] Inventor: Nalinkant C. Damani, Mountain View, Calif.

[73] Assignee: Alza Corporation, Palo Alto, Calif.

[ * ] Notice: The portion of the term of this patent subsequent to Aug. 27, 1991, has been disclaimed.

[22] Filed: July 21, 1975

[21] Appl. No.: 597,568

Related U.S. Application Data

[60] Continuation of Ser. No. 477,990, June 10, 1974, which is a division of Ser. No. 409,243, Oct. 24, 1973, Pat. No. 3,831,606, which is a continuation of Ser. No. 117,015, Feb. 19, 1971, abandoned.

[52] U.S. Cl. ............................... 128/266; 128/206
[51] Int. Cl.[2] ................. A61M 15/08; A61M 13/00
[58] Field of Search .................... 128/206, 208, 266; 222/193

[56] References Cited

UNITED STATES PATENTS

| | | | |
|---|---|---|---|
| 2,573,918 | 11/1951 | McCuiston ......................... | 128/206 |
| 2,946,332 | 7/1960 | Sacks ................................. | 128/266 |
| 3,507,277 | 4/1970 | Altounyan et al. ................ | 128/208 |
| 3,831,606 | 8/1974 | Damani .............................. | 128/266 |

Primary Examiner—Aldrich F. Medbery
Attorney, Agent, or Firm—Thomas E. Ciotti; Paul L. Sabatine; Edward L. Mandell

[57] ABSTRACT

A process for dispensing medicaments in aerosol form for inhalation therapy is disclosed. The process comprises: providing a hollow elongate housing having air inlet and air outlet passages; generating a positive pressure, air-stream between the inlet and outlet passages; rotationally releasing medicament from a container within the housing into the air-stream; and inserting the outlet passage into the oral or nasal cavity of the patient.

8 Claims, 3 Drawing Figures

MEDICAMENT DISPENSING PROCESS FOR INHALATION THERAPY

This is a continuation of application Ser. No. 477,990 filed June 10, 1974, which in turn is a division of application Ser. No. 409,243 filed Oct. 24, 1973 now U.S. Pat. No. 3,831,606, issued Aug. 27, 1974, which in turn is a continuation of application Ser. No. 117,015 filed Feb. 19, 1971 and now abandoned.

BACKGROUND OF THE INVENTION

This invention relates to the administration of drugs to a patient via inhalation through the oral and/or nasal passages, and more especially to a device which propels a uniform dosage of finely divided medicament into the lungs through the aforementioned passages.

In the past, administration of medicaments for the alleviation of ailments of the lungs has been carried out using plastic squeeze bottles or aerosol cans to deliver drugs through the oral and/or nasal cavities. Devices of this type have not been entirely satisfactory because they do not allow the user to properly control the medicament concentration or dosage. Furthermore, significant problems arise as a result of the variation in particle size of the medicament spray delivered from these devices. Thus, it is not always possible with these devices to dispense a medicament in the form of very fine and uniform particle size or mist which can be readily inhaled by the user. Sonic generators have proven to be the only truly effective devices for accomplishing complete control of both medicament dosage and particle size; however, these are extremely large and can be used only in a hospital, doctor's office, clinic, etc. There have also been attempts to provide smaller, pocket-sized inhalation devices which may be used in any location to supply the necessary medication. Many of these personal sized devices are based upon aerosol principles (see for example, U.S. Pats. No. 3,183,907, No. 3,456,645, and No. 3,456,646) and of necessity suffer from the aforementioned disadvantages associated with aerosolized atomizers. More recent endeavors in the area of pocket size atomizers are exemplified by U.S. Pats. No. 3,507,277 and 3,518,992 wherein the medicament is placed in the inhaler in capsulized form, made of gelatin or other material, and thereafter the capsule is perforated in situ to render the medicament available immediately prior to its contemplated use. The user then inhales through the device which causes an internally contained propeller, as well as the punctured capsule, to rotate thereby dispensing the medicament from the device and into the oral or nasal passages of the user. While these latter type of devices may solve the heretofore mentioned medicament dosage and particle size problems, they too are rendered not wholly effective because typically those people having ailments necessitating the subject medication, as for example asthmatic patients, cannot efficiently draw air through their oral or nasal passages, and, as a result, they often cannot administer to themselves the entire medicament dosage. In fact, those persons most in need of the drug are those who are least able to draw air, and hence medicament, through the device.

SUMMARY OF THE INVENTION

Accordingly, it is a primary object of this invention to provide an inhalation device which is capable of dispensing a precise quantity of medicament in extremely uniform particle size to any patient regardless of his ability to inhale.

Another object of this invention is to provide an improved inhalation device which can deliver in uniform particle size a medicament in either liquid, microencapsulated, or dry powder form without the use of Freon or similar aerosolizing material.

In attaining the objects of this invention, one feature resides in a device for the oral inhalation of medicaments in finely divided form which comprises a hollow elongate housing having one end adapted for insertion into the oral or nasal cavity of a user. The end so-adapted is provided with at least one air passageway therein, and there is provided at least one other air passageway near the other end of the housing. Inside the housing there is rotatably mounted a propeller means, and attached thereto is a mounting means for receiving a container of medicament. The device also contains one or more piercing members for perforating the container while it is contained in the aforementioned mounting means, such piercing members typically being spring-biased or loaded. The device is particularly characterized by a self-contained power source for operating the propeller means via external manual manipulation by the user. One such power source comprises an electric motor, battery and external switch combination, while an alternative embodiment includes a threaded plunger arrangement. In a further embodiment the device contains an atomizing means rotatably mounted inside the housing intermediate the medicament container mounting means and the housing end adapted for insertion into the oral or nasal cavity of a user. This atomizer is employed when the medicament is present in other than dry particulate form. In a typical embodiment, the spring-loaded piercing members include exteriorly located push button means attached thereto allowing the user to press the piercing members into the medicament container.

DETAILED DESCRIPTION OF THE INVENTION

Figure 1:
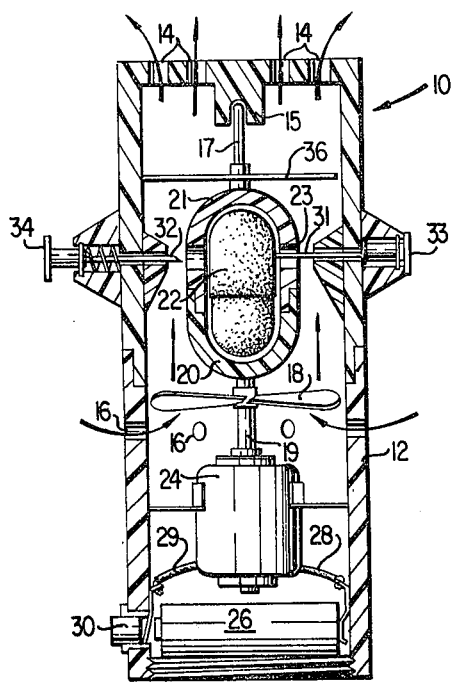
FIG. 1 is a cross-sectional view of an oral inhalation device according to this invention wherein the power source is an electric motor.
Figure 2:
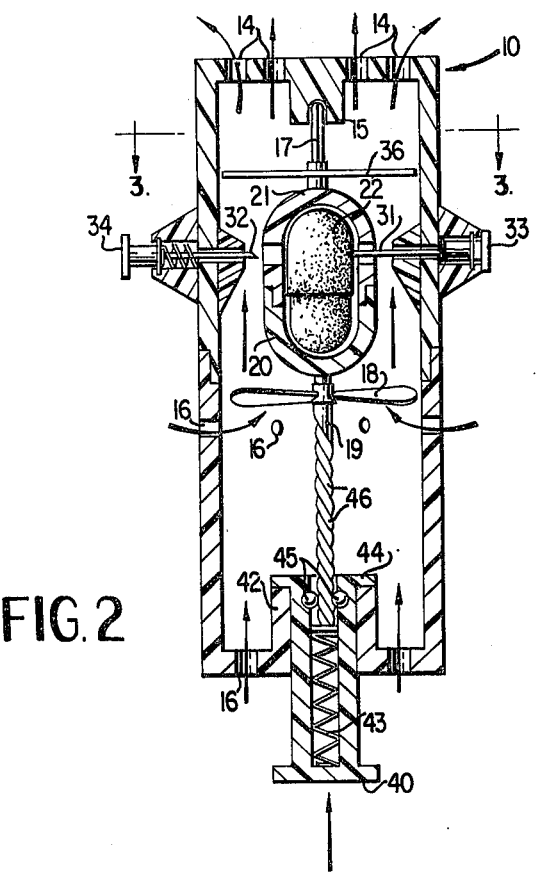
FIG. 2 is a cross-sectional view of another embodiment of the present invention wherein a plunger is employed as the power source.
Figure 3:
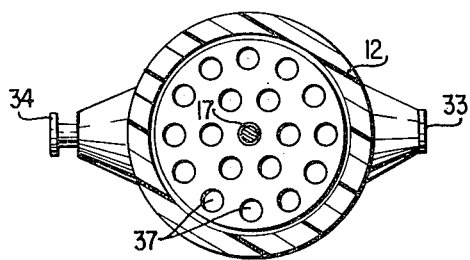
FIG. 3 is a view along the line 3—3 in FIG. 2 illustrating an atomizer disc which may optionally be included in the devices of this invention.

In one embodiment in accordance with this invention, as illustrated in FIG. 1, an oral inhalation device 10 is comprised of a rigid, hollow cylindrical housing 12 having its upper end adapted for insertion into the oral or nasal cavity of a user. Located in the upper end wall are a plurality of passageways 14 communicating with the inside of the housing and allowing free passage of air and medicament therethrough. Near the lower end of the housing 12 are located another series of similar passageways 16 providing for the ingress of air into the inhalation device. Propeller 18 is rotatably mounted on shaft 19 inside of housing 12. Immediately above propeller 18 and likewise connected to shaft 19 is a cup-like mounting means 20 for receiving a container of medicament such as capsule 22. This entire assembly comprised of mounting means 20, propeller 18 and shaft 19 is driven by a small battery powered electric motor 24 secured to housing 12 immediately beneath the indicated assembly. A battery 26, typically size N or smaller, is also contained within housing 12 and is connected to motor 24 through conductors 28 and 29. Selective operation of motor 24 is achieved through operation of push button 30 located on the exterior of housing 12 adjacent to battery 26.

In the sidewall portions of housing 12 immediately adjacent medicament container mounting means 20 are located two spring-loaded piercing members 31 and 32 by means of which the user may pierce the medicament container 22, while in its supporting member 20, immediately prior to desired use of the device. The piercing members are conveniently actuated by the push button members 33 and 34 connected thereto on the external side of housing 12; however, other actuating means may also be employed for this purpose. For purposes of illustration, one assembly is shown in the non-piercing position whereas the other assembly is shown with the tip of piercing member 31 having pierced capsule 22. Preferably, the perforating ends of piercing members 31 and 32 are sharpened with a plane face at an acute angle, and furthermore, the acute angled plane face desirably faces away from propeller 18. Actuation of the piercing members advantageously provides one or more holes, suitably of about 0.6 to 0.65 mm. in diameter, in the capsule wall. It will of course be appreciated that any other suitable medicament container piercing assembly may be employed in the devices of this invention, for example, one such as that disclosed in U.S. Pat. No. 3,518,992.

Medicament containing capsule 22 can be a standard capsule of gelatin or other material having the medicament contained therein in either dry powder, microencapsulated, or liquid form. After piercing of the capsule walls has taken place, medicament will be forced out of the capsule into the air stream created by propeller 18 as a result of the forces created by the rotational movement of the capsule itself.

When the medicament in capsule 22 is in liquid form, and in certain other instances, it is desired to further employ an atomizing disc 36 between the medicament container mounting means 20 and the medicament dispensing end of the device. The atomizing disc 36 is secured to shaft 17 and the resultant assembly is likewise secured to inverted cup-like member 21 which may be removably engaged over cup-like mounting member 20 which receives and holds the medicament capsule 22. Thus, inverted cup-like member 21 rotates together with mounting means 20, and as a result, atomizing disc 36 is likewise caused to rotate. For support and stabilization, shaft 17 loosely engages with bearing member 15 contained in housing 12. Inverted cup-like member 21 advantageously is of a cage-like configuration having only a few relatively narrow support members (preferably having no two support members lying on any one diameter across member 21) thereby providing openings 23 around substantially the entire circumference of member 21 to facilitate easy entrance by piercing members 31 and 32.

A planar view of atomizer disc 36 is illustrated in FIG. 3. The disc contains a plurality of apertures 37 uniformly distributed thereover, the same being for the purpose of assuring substantially uniform medicament particle size when capsule 22 contains medicament in the form of a liquid or any other form which is likely to agglomerate.

Referring now to FIG. 2, there is illustrated an alternative embodiment of the oral inhalation device of the invention. The portion of the device extending from propeller 18 to the medicament dispensing end of the device is essentially identical to the corresponding portion of the device illustrated in FIG. 1. In FIG. 2, a spring-loaded plunger assembly is employed as the power source in lieu of the battery operated electric motor illustrated in FIG. 1. The plunger assembly consists of plunger 40 slidably mounted in sleeve 42 at the lower end wall of housing 12. Plunger 40 is biased downwardly by spring 43 and retained in the device by cooperation of flange 44 with sleeve 42. Near the upper end of plunger 40 are located a plurality of ball bearings 45 which are freely rotatable and cooperate with threads 46 contained on the lower portion of shaft 19. Thus, when plunger 40 is depressed into housing 12, ball bearings 45 travel upwardly in threads 46 causing rotation of shaft 19 and hence propeller 18, medicament container support 20 and optionally atomizing disc 36. It will be appreciated that suitable gearing linkages may be incorporated into the plunger assembly to selectively vary the amount of rotation generated by each depression of plunger 40.

In operation, the two sections of housing 12 are separated and a container of medicament, such as a capsule, is placed into support 20. At this time, the atomizer disc assembly may be inserted or removed as desired. The housing is again closed, and the device may now be carried by the user for an indefinite period of time without deterioration or loss of medicament. When the administration of medicament is required, the user depresses push buttons 33 and 34 to puncture the capsule in situ, and thereafter places the dispensing end of the device into his oral or nasal cavity, whereupon medicament may then be dispensed by either activation of electric motor 24 via push button 30 or depression of plunger 40.

The drug present in capsule 22 may be either a single or multiple dosage. For a single dosage, the device is constructed so that all of the medicament is delivered with a single push of the plunger 40 or depression of switch 30. In the case of a multiple dosage containing capsule, the device may be designed to administer only a single dose on each push of plunger 40 or timed depression of button 30. Repetition of this action similarly delivers the second and subsequent doses of the medicament. The embodiment illustrated in FIG. 2 is especially suited for such a modification.

Thus, the invention provides an oral inhalation device suitable for the administration of exact dosages of medicaments in finely divided form for the alleviation of ailments of the bronchial tract and of the lungs. The device may also be used for the administration of medicaments having systemic action, for example, it may be used for the administration of an antidote to poisonous substances. The device provides a simple method of carrying medicaments which require rapid or emergency usage, and moreover the device assures that a uniform dosage of such a medicament is administered regardless of the user's ability to properly inhale.

While the invention has been described and illustrated with reference to certain preferred embodiments thereof, those skilled in the art will appreciate that various modifications, changes, omissions and substitutions can be made without departing from the spirit of the invention. It is intended, therefore, that the invention be limited only by the scope of the following claims.

What is claimed is:

1. A process of dispensing medicament for inhalation by a patient comprising:
   a. providing a hollow elongate housing having air inlet and air outlet passages;
   b. mounting a closed container of medicament within the housing on a fixed axis of rotation;
   c. opening said container;
   d. operating an internal rotation producing means to generate a positive pressure air stream between the air inlet and the air outlet to discharge the air stream from the outlet;
   e. rotating the container of medicament about said axis within the housing by said rotation producing means;
   f. dispensing a dosage of medicament from the container into the airstream while the container is rotating; and
   g. inserting the air outlet passage into the oral or nasal cavity of the patient.

2. The process of claim 1 wherein the medicament is dispensed into the airstream in a finely divided solid form.

3. The process of claim 1 wherein the medicament is dispensed into the airstream in liquid form and the process includes:
   h. passing the liquid medicament through an atomizer disposed within the housing between the medicament dispensing site and the air outlet passage.

4. The process of claim 1 wherein the airstream is generated by an electrically driven propeller positioned in the housing.

5. The process of claim 1 wherein the airstream is generated by a hand driven propeller positioned in the housing.

6. The process of claim 1 wherein the container is opened by piercing the container.

7. The process of claim 1 wherein the container contains a plurality of doses of medicament and the airstream is generated intermittently with a single dose of medicament being dispensed with each occurrence of the generation of the airstream.

8. The process of claim 1 wherein the airstream is generated continuously.

* * * * *